United States Patent
Omi (10) Patent No.: US 10,095,914 B2
(45) Date of Patent: Oct. 9, 2018

(54) IMAGE PICKUP DEVICE, NEAR INFRARED LIGHT EMISSION DEVICE, AND SUNVISOR

(71) Applicant: DENSO CORPORATION, Kariya, Aichi-pref. (JP)

(72) Inventor: Takuhiro Omi, Anjo (JP)

(73) Assignee: DENSO CORPORATION, Kariya (JP)

( * ) Notice: Subject to any disclaimer, the term of this patent is extended or adjusted under 35 U.S.C. 154(b) by 237 days.

(21) Appl. No.: 14/648,012

(22) PCT Filed: Nov. 18, 2013

(86) PCT No.: PCT/JP2013/006744
§ 371 (c)(1),
(2) Date: May 28, 2015

(87) PCT Pub. No.: WO2014/103141
PCT Pub. Date: Jul. 3, 2014

(65) Prior Publication Data
US 2015/0310258 A1 Oct. 29, 2015

(30) Foreign Application Priority Data
Dec. 24, 2012 (JP) .................. 2012-280414

(51) Int. Cl.
*G06K 9/00* (2006.01)
*B60J 3/02* (2006.01)
(Continued)

(52) U.S. Cl.
CPC ............ *G06K 9/00255* (2013.01); *A61B 5/18* (2013.01); *B60J 3/007* (2013.01); *B60J 3/0234* (2013.01);
(Continued)

(58) Field of Classification Search
CPC .... G08B 21/06; G06K 9/00845; B60Q 3/252; B60R 11/04; H04N 5/332
See application file for complete search history.

(56) References Cited

U.S. PATENT DOCUMENTS

2006/0018641 A1  1/2006  Goto et al.
2007/0176402 A1  8/2007  Irie et al.
(Continued)

FOREIGN PATENT DOCUMENTS

DE   102006006690 A1   8/2007
JP   62-015046 U        1/1987
(Continued)

OTHER PUBLICATIONS

International Search Report and Written Opinion of the International Searching Authority dated Feb. 18, 2014 issued in the corresponding International application No. PCT/JP2013/006744 (and English translation).

*Primary Examiner* — Gims S Philippe
*Assistant Examiner* — Mainul Hasan
(74) *Attorney, Agent, or Firm* — Posz Law Group, PLC (57) ABSTRACT

An image pickup device includes a first emission unit that emits a near infrared light toward a face of a driver from a front lower side of the driver, and a second emission unit that emits a near infrared light from an upper side of the driver. When a sunvisor is present at a storage position in which sunlight is not shielded, the second emission unit is disposed at a position to be covered with the sunvisor. A portion where the sunvisor present at a storage position covers the second emission unit is made of a material that shields a visible light contained in the sunlight and transmits the near infrared light.

7 Claims, 10 Drawing Sheets

(51) Int. Cl.
- *B60Q 3/00* (2017.01)
- *B60J 3/00* (2006.01)
- *B60R 11/04* (2006.01)
- *H04N 5/33* (2006.01)
- *A61B 5/18* (2006.01)
- *G08B 21/06* (2006.01)
- *B60Q 3/252* (2017.01)
- *B60Q 3/76* (2017.01)
- *A61B 5/11* (2006.01)
- *B60R 11/00* (2006.01)

(52) U.S. Cl.
CPC .............. *B60Q 3/252* (2017.02); *B60Q 3/76* (2017.02); *B60R 11/04* (2013.01); *G06K 9/00845* (2013.01); *G08B 21/06* (2013.01); *H04N 5/332* (2013.01); *A61B 5/1103* (2013.01); *B60J 3/0278* (2013.01); *B60R 2011/0005* (2013.01)

(56) References Cited

U.S. PATENT DOCUMENTS

| | | | |
|---|---|---|---|
| 2009/0050807 A1 | 2/2009 | Ota et al. | |
| 2009/0091821 A1* | 4/2009 | Regan | G02B 5/208 |
| | | | 359/351 |
| 2013/0026233 A1* | 1/2013 | Chen | G06K 7/10722 |
| | | | 235/440 |

FOREIGN PATENT DOCUMENTS

| | | | | |
|---|---|---|---|---|
| JP | 2005-247014 A | | 9/2005 | |
| JP | 2005-271875 A | | 10/2005 | |
| JP | 2005-271876 A | | 10/2005 | |
| JP | 2005271876 A | * | 10/2005 | |
| JP | 2005271876 A | * | 10/2005 | |
| JP | 2009-161143 A | | 7/2009 | |
| JP | 2010-076572 A | | 4/2010 | |
| JP | 2010-269738 A | | 12/2010 | |

\* cited by examiner

IMAGE PICKUP DEVICE, NEAR INFRARED LIGHT EMISSION DEVICE, AND SUNVISOR

CROSS REFERENCE TO RELATED APPLICATIONS

The present disclosure is a U.S. national stage of International Application No. PCT/JP2013/006744 filed on Nov. 18, 2013 and is based on and claims priority to Japanese Patent Application No. 2012-280414 filed Dec. 24, 2012, the contents of which are incorporated herein by reference.

TECHNICAL FIELD

The present disclosure relates to an image pickup device, a near infrared light emission device, and a sunvisor which capture an image of a face of a driver with the use of a near infrared light.

BACKGROUND ART

A technique for analyzing the image of the face of the driver which is captured by using the near infrared light to detect the arousal level and inattentive driving of the driver and to utilize detection results for drive assist has been proposed. In order to detect the arousal level and the inattentive driving with high precision, it is desirable to capture the image of the face of the driver under a stable condition. However, when the image is captured relying on the near infrared light contained in sunlight, a condition under which the face of the driver is illuminated changes depending on weather or a time zone.

Under the circumstances, providing a first emission unit in the vicinity of a camera for capturing the image of the face, and emitting a near infrared light diagonally upward toward the face of the driver has been extensively conducted. With the above configuration, since the near infrared light can be always emitted from the first emission unit under the same condition, the face of the driver can be illuminated under the relatively similar condition regardless of the weather or the time zone. However, since the first emission unit illuminates the face from a lower side of the face, the amount of light in an upper side of the face is likely to become insufficient due to only the first emission unit. Further, when the face is illuminated from one direction, a shade is likely to be produced in the captured image. Under the circumstances, a technique for incorporating a second emission unit into the sunvisor to emit the near infrared light toward the face also from an upper side of the driver has been also proposed (PTL 1).

However, when the second emission unit that emits the near infrared light is incorporated into the sunvisor, such problems that not only a structure of the sunvisor is complicated, but also a harness for supplying power to the second emission unit of the sunvisor is required and a workload for assembling the harness is caused occur.

PRIOR ART LITERATURES

Patent Literature

PTL 1: JP 2005-271876 A

SUMMARY OF INVENTION

It is an object of the present disclosure to provide a technique in which an image of a face of a driver can be captured with the emission of a near infrared light simply and under a stable condition.

An image pickup device according to one aspect of the present disclosure is mounted on a vehicle and captures an image of a driver of the vehicle. The image pickup device includes a face image pickup unit, a first emission unit, a sunvisor, and a second emission unit. The face image pickup unit is arranged in front of a driver seat of the vehicle, and captures an image of a face of the driver from a front side of the driver. The first emission unit is arranged in front of the driver seat of the vehicle and emits a near infrared light toward the face from a front lower side of the driver. The sunvisor is fitted to an upper side of the driver seat in a vehicle interior, and is movable between a light shielding position at which sunlight to the face is shielded and a storage position at which the sunlight to the face is not shielded. The second emission unit is located at a position where the second emission unit is covered with the sunvisor when the sunvisor is present at the storage position, but is not covered with the sunvisor when the sunvisor is present at the light shielding position. The second emission unit emits a near infrared light toward the face of the driver. In the sunvisor, a portion that covers the second emission unit when the sunvisor is located at the storage position is made of a material that shields a visible light contained in the sunlight and transmits the near infrared light.

The image pickup device can capture the image of the face of the driver under the stable condition without being affected by the weather or the time zone.

A near infrared light emission device according to another aspect of the present disclosure is mounted on a vehicle and emits a near infrared light toward a face of a driver of the vehicle. The near infrared light emission device includes a first emission unit, a sunvisor, and a second emission unit. The first emission unit is arranged in front of the driver seat of the vehicle and emits a near infrared light toward the face from a front lower side of the driver. The sunvisor is fitted to an upper side of the driver seat in a vehicle interior and is movable between a light shielding position at which sunlight to the face is shielded and a storage position at which the sunlight to the face is not shielded. The second emission unit is located at a position where the second emission unit is covered with the sunvisor when the sunvisor is present at the storage position, but is not covered with the sunvisor when the sunvisor is present at the light shielding position. The second emission unit emits a near infrared light toward the face of the driver. In the sunvisor, a portion that covers the second emission unit when the sunvisor is located at the storage position is made of a material that shields a visible light contained in the sunlight and transmits the near infrared light.

The near infrared light emission device can emit the near infrared light to the face of the driver under the stable condition without being affected by the weather or the time zone.

A sunvisor according to another aspect of the present disclosure is fitted to a vehicle interior of a vehicle and shields sunlight to a face of a driver of the vehicle. The sunvisor includes a main body part and an attaching part. The main body part is made of material that shields the sunlight. The attaching part attaches the main body part to the vehicle interior in a state to be movable between a light shielding position at which the sunlight to the face is shielded and a storage position at which the sunlight to the face is not shielded. The main body part is provided with a transmission window made of a material that shields a visible light contained in the sunlight and transmits the near infrared light.

With the above configuration, the near infrared light can be emitted toward the face of the driver from the transmission window over the sunvisor in a state where the sunvisor is present at the storage position.

BRIEF DESCRIPTION OF DRAWINGS

The above and other objects, features and advantages of the present disclosure will become more apparent from the following detailed description made with reference to the accompanying drawings. In the drawings.

EMBODIMENTS FOR CARRYING OUT INVENTION

Figure 1:
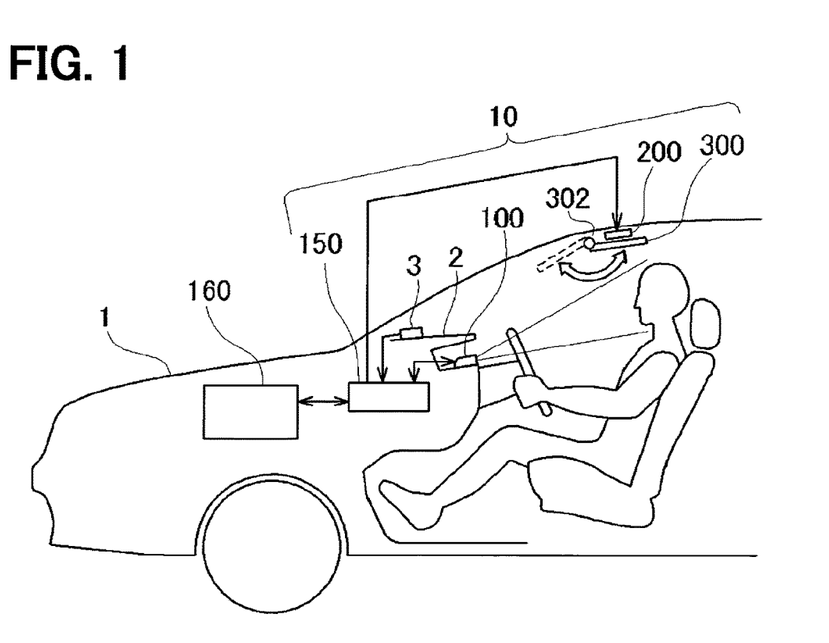
FIG. 1 is a diagram illustrating a vehicle on which an image pickup device according to an embodiment of the present disclosure is mounted.

An image pickup device 10 according to an embodiment of the present disclosure will be described with reference to FIG. 1. FIG. 1 illustrates a rough configuration of a vehicle 1 on which the image pickup device 10 is mounted. The image pickup device 10 includes an image pickup unit 100 that is mounted on a dashboard 2 at the rear side of a steering column when viewed from a driver, an auxiliary illumination unit 200 that is assembled into a vehicle interior (for example, a ceiling portion) above the driver, a sunvisor 300 that is fitted to the vehicle interior so as to cover the auxiliary illumination unit 200, and an image pickup control unit 150 that is mounted in the dashboard 2. A solar radiation sensor 3 is also mounted on the dashboard 2.

Among those components, the image pickup unit 100 captures an image of a face of the driver at an angle (about 20 to 30 degrees in elevation) at which to look up at the face from a front lower side of the driver. The sunvisor 300 is attached to the ceiling portion of the vehicle 1 in the vehicle interior through a hinge 302, and the driver rotates the sunvisor 300 at a portion of the hinge 302, thereby being capable of shielding the sunlight. In FIG. 1, the sunvisor 300 that is in a state where the sunlight is not shielded (state at a storage position) is indicated by a bold solid line, and the sunvisor 300 that is in a state where the sunlight is shielded (state at a light shielding position) is indicated by a thin dashed line. In the following description, a state in which the sunvisor 300 is at the storage position may be called "closed state", and a state in which the sunvisor 300 is at the light shielding position may be called "open state".

When the sunvisor 300 is present at the storage position (closed state), the overall auxiliary illumination unit 200 is covered with the sunvisor 300, and is not viewed from the driver. However, when the sunvisor 300 rotates and moves to the light shielding position (put into the open state), the covered auxiliary illumination unit 200 appears, and a visible light can be emitted to the driver. The solar radiation sensor 3 is mounted on the dashboard 2 at a position where the sunlight is well irradiated, detects the amount of solar radiation, and outputs the detected amount of solar radiation to an image pickup control unit 150. The image pickup control unit 150 is a microcomputer configured by connecting a ROM, a RAM and the like around a CPU by a bus, and controls the operation of capturing the image of the face of the driver by the image pickup unit 100. Although described in detail later, the image pickup control unit 150 also controls the operation of illuminating the face of the driver with the use of the image pickup unit 100 and the auxiliary illumination unit 200 when capturing the image of the face of the driver.

As illustrated in FIG. 1, a monitoring control unit 160 that monitors a state of the driver on the basis of the image of the face of the driver is also mounted on the vehicle 1 of the present embodiment. The monitoring control unit 160 is a microcomputer configured by connecting a ROM, a RAM and the like around a CPU by a bus. Upon acquiring the image of the face of the driver from the image pickup control unit 150, the monitoring control unit 160 detects the degree of opening of eyelids, the frequency of blinking, or eye movement to monitor an arousal level of the driver.

Figure 2:
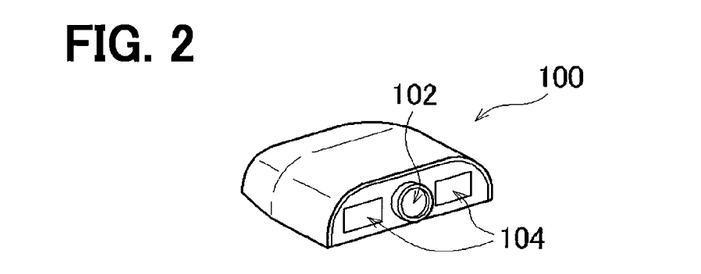
FIG. 2 is a perspective view illustrating an external shape of an image pickup unit mounted on the vehicle.

FIG. 2 illustrates an external shape of the image pickup unit 100. An image pickup unit 102 is mounted in the center of the image pickup unit 100, and first emission units 104 that emit near infrared light are mounted on both of right and left sides of the image pickup unit 102. An optical filter (near infrared light transmission filter) made of methacrylic resin not shown, which does not transmit the light of a wavelength in a visible light region, but transmits the light of a wavelength longer than the near infrared region, is incorporated in the image pickup unit 102. A solid-state image sensing element such as a CMOS or a CCD not shown is mounted at the rear side of the optical filter. Accordingly, since the near infrared light reaches the solid-state image sensing element, an image caused by the near infrared light is entirely captured by the image pickup unit 102. A material of the optical filter is not limited to methacrylic resin, but may be another resin such as polycarbonate resin.

A near infrared light LED not shown that emits the near infrared light, and a near infrared light transmission filter not shown are mounted in the first emission units 104. After the light from the near infrared light LED has passed through the near infrared light transmission filter, the light is emitted from the first emission units 104 to the external. Thus, even if the light of a visible light component is slightly emitted from the near infrared light LED, most of the light is cut off by the near infrared light transmission filter, and the near infrared light that cannot be sensed by a person is emitted toward the face of the driver from the first emission units 104. In the present embodiment, the image pickup unit 102 of the image pickup unit 100 corresponds to the face image pickup unit.

Figure 3A:
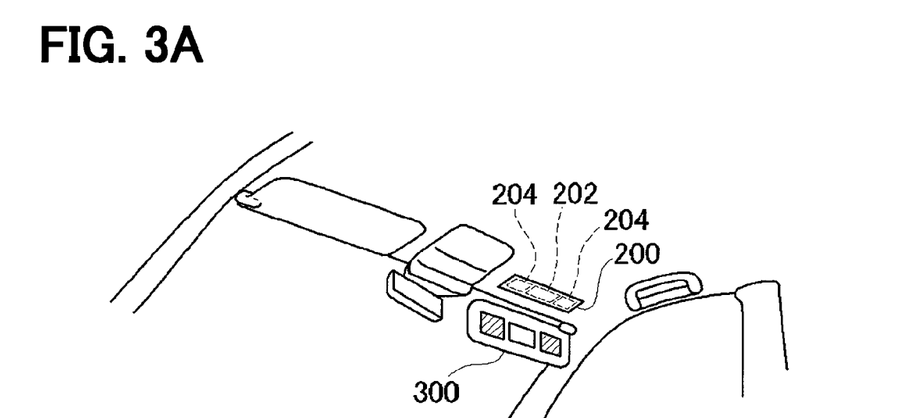
FIG. 3A is a diagram illustrating an auxiliary illumination unit and a sunvisor mounted on an upper side of a driver seat in a vehicle interior.

FIG. 3A illustrates a state in which the auxiliary illumination unit 200 is mounted on the ceiling portion of the vehicle interior. As described above, when the sunvisor 300 is present at the storage position (closed state) not to shield the sunlight, the auxiliary illumination unit 200 is covered with the sunvisor 300. Thus, in FIG. 3A, the sunvisor 300 is put into a state (closed state) in which the sunvisor 300 is rotated to the position (light shielding position) where the sunlight is shielded to indicate the auxiliary illumination unit 200.

As illustrated in FIG. 3A, the auxiliary illumination unit 200 according to the present embodiment is roughly formed into a horizontally long rectangular shape, and an illumination unit 202 that emits a visible light is disposed in the center portion. Thus, when the sunvisor 300 is put into the open state, and the visible light is emitted from the illumination unit 202, the face and hands of the driver can be brightly illuminated. The illumination unit 202 of the auxiliary illumination unit 200 is used to illuminate documents at hand and confirm the contents thereof by the driver, or in the case of a woman, the illumination unit 202 is used to fix makeup with a small mirror attached to the sunvisor 300. In the auxiliary illumination unit 200 according to the present embodiment, second emission units 204 that emit the near infrared light are disposed on both of the right and left sides of the illumination unit 202. Although described in detail later, the second emission units 204 are used to emit the near infrared light toward the face of the driver from the upper side in capturing the image of the face of the driver by the image pickup unit 102 of the image pickup unit 100.

Figure 3B:
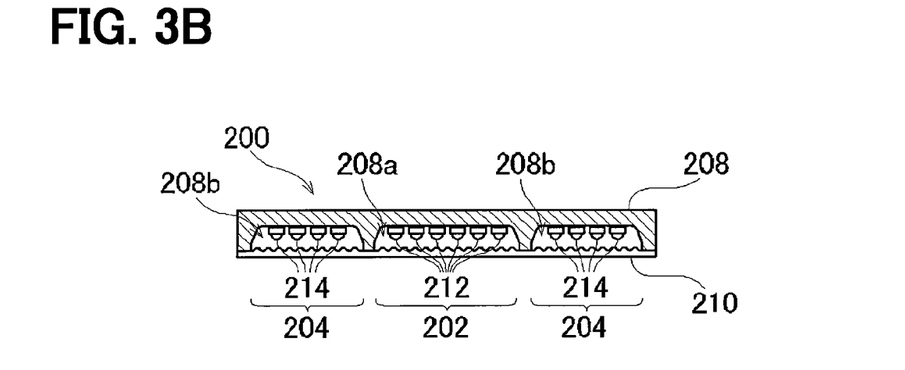
FIG. 3B is a cross-sectional view of the auxiliary illumination unit.

FIG. 3B illustrates a rough internal structure by taking a cross-section of the auxiliary illumination unit 200. Three large concave portions 208a and 208b are formed in a row in a bottom of a main body case 208 of the auxiliary illumination unit 200. Visible light LEDs 212 that emit the visible light are arranged in the center concave portion 208a, and near infrared light LEDs 214 that emit near infrared light are arranged in the two concave portions 208b on both sides of the main body case 208. The overall bottom of the main body case 208 is covered with a diffuser panel 210 made of a transparent resin material to form the auxiliary illumination unit 200. In the diffuser panel 210 that covers the bottom of the main body case 208, a portion that covers the center concave portion 208a configures the illumination unit 202, and portions that cover the concave portions 208b on both sides configure the second emission units 204.

Figure 4:
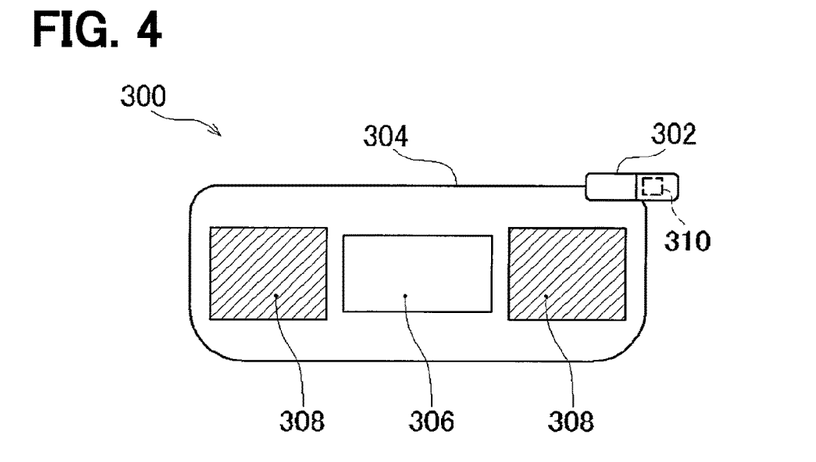
FIG. 4 is a diagram illustrating a structure of the sunvisor.

FIG. 4 illustrates a rough structure of the sunvisor 300 according to the present embodiment. FIG. 4 illustrates a state in which the sunvisor 300 is viewed from the driver seat side in a state where the sunvisor 300 rotates to a vertical position (see FIG. 3A). The sunvisor 300 includes a main body part 304 having a substantially horizontally long rectangular shape, the hinge 302 that is fitted to a corner of an upper side of the main body part 304, and a small mirror 306 that is fitted to the center of a surface facing the driver when the sunvisor 300 is put into the open state. Among those components, the hinge 302 is fitted to the ceiling portion of the vehicle 1 in the vehicle interior to support the main body part 304 in a cantilever state. An open/close switch 310 that is turned off when the sunvisor 300 becomes in the closed state and is turned on when the sunvisor 300 becomes in the open state is mounted in the hinge 302. In the present embodiment, the hinge 302 corresponds to the attaching part, and the open/close switch 310 corresponds to a detection unit.

The main body part 304 of the sunvisor 300 is made of an opaque material that transmits none of the visible light and the near infrared light. Transmission windows 308 are formed on both of the right and left sides of a portion of the sunvisor 300 to which the small mirror 306 is attached. In the transmission windows 308, near infrared light transmission filters made of methacrylic resin that transmits partial wavelengths of the near infrared light are fitted into both of the right and left sides. A material of the near infrared light transmission filter is not limited to the methacrylic resin, but may be another resin such as polycarbonate resin. When the sunvisor 300 rotates from the "open state" illustrated in FIG. 3A into the "closed state", the portion to which the small mirror 306 is attached covers the illumination unit 202 of the auxiliary illumination unit 200, and the transmission windows 308 formed on both sides thereof cover the second emission units 204 of the auxiliary illumination unit 200.

Figure 5:
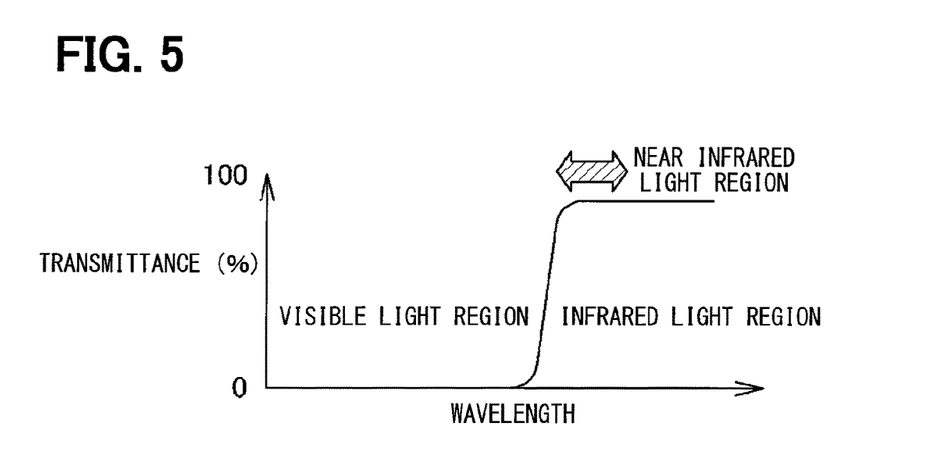
FIG. 5 is a diagram exemplifying a light transmission characteristic of a transmission window provided in the sunvisor.

FIG. 5 exemplifies a transmittance of the near infrared light transmission filter fitted into the respective transmission windows 308. As illustrated in the figure, the near infrared light transmission filter has a property of hardly transmitting the light of the visible light region, but transmitting 90% or more of the light having the partial wavelength of the near infrared light region and the wavelength of the infrared light region. Thus, even when the sunvisor 300 is in the closed state, if the near infrared light is emitted from the second emission units 204 of the auxiliary illumination unit 200, the near infrared light can be emitted to the driver through the transmission windows 308 of the sunvisor 300.

Figure 6:
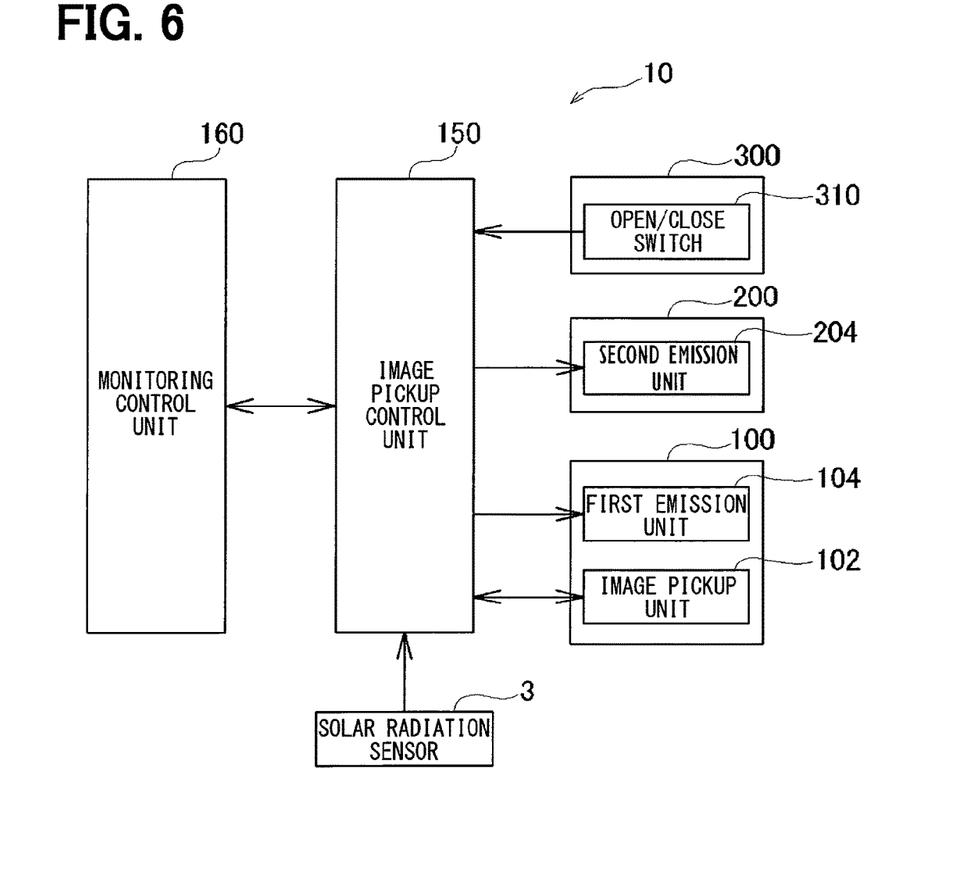
FIG. 6 is a block diagram illustrating a configuration of the image pickup device.

FIG. 6 illustrates a block diagram of the image pickup device 10 according to the present embodiment. The image pickup unit 102 of the image pickup unit 100 is connected to the image pickup control unit 150 to enable data transfer with respect to the image pickup control unit 150. When the image pickup unit 102 captures an image on the basis of a control signal from the image pickup control unit 150, the image pickup unit 102 outputs the obtained image data to the image pickup control unit 150. When the first emission units 104 of the image pickup unit 100 and the second emission units 204 of the auxiliary illumination unit 200 emit the near infrared light upon receiving a drive signal from the image pickup control unit 150. The image pickup control unit 150 is also connected with the open/close switch 310 of the sunvisor 300 and the solar radiation sensor 3. The image pickup control unit 150 can detect an open/close state of the sunvisor 300 on the basis of an output from the open/close switch 310, and can detect brightness around the vehicle 1 and the intensity of sunlight on the basis of an output from the solar radiation sensor 3. A configuration (that is, configuration except for the image pickup unit 102 of the image pickup unit 100) for emitting the near infrared light in the image pickup device 10 according to the present embodiment corresponds to the near infrared light emission device.

The image pickup control unit 150 and the monitoring control unit 160 are connected to each other so as to enable data transfer therebetween, and the image pickup control unit 150 outputs image data captured by the image pickup unit 102 to the monitoring control unit 160.

Figure 7:
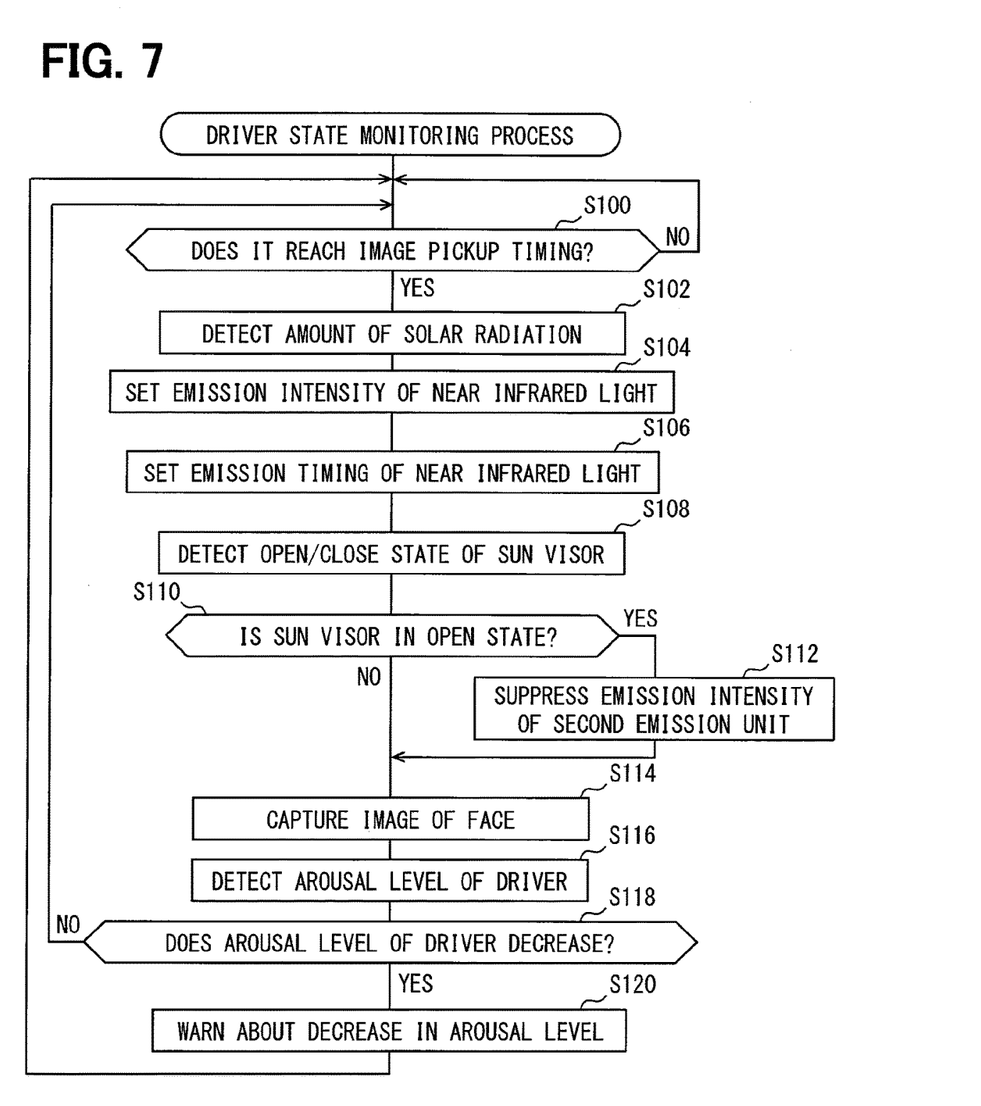
FIG. 7 is a flowchart illustrating a driver state monitoring process.

A driver state monitoring process executed by the image pickup control unit 150 and the monitoring control unit 160 according to the present embodiment will be described with reference to FIG. 7. First of all, it is determined whether to reach image pickup timing of the driver, or not (S100). A timer not shown is incorporated into the image pickup control unit 150, the image of the face of the driver is captured at predetermined intervals of about 30 msec, and the arousal level of the driver is detected by analyzing plural images captured at the predetermined intervals. Therefore, if the predetermined interval does not elapse after the image has been captured previously, it is determined not to reach the image pickup timing (NO in S100), and the same determination is repeated into a standby state.

If it is determined to reach the image pickup timing (YES in S100), the amount of solar radiation is detected according to an output from the solar radiation sensor 3 (S102). The emission intensity of the near infrared light is set for each of the first emission units 104 of the image pickup unit 100 and the second emission units 204 of the auxiliary illumination unit 200 on the basis of the detected amount of solar radiation (S104). For example, if the amount of solar radiation detected by the solar radiation sensor 3 is large, it is conceivable that the amount of near infrared light contained in the sunlight is large. Therefore, the emission intensity of the near infrared light of the first emission units 104 and the second emission units 204 is set to be lower. Conversely, if the amount of solar radiation is small, the emission intensity of the near infrared light of the first emission units 104 and the second emission units 204 is set to be higher so as to compensate a reduction in the near infrared light contained in the sunlight. With the above setting, the driver can be illuminated with the near infrared light of the similar intensity regardless of the brightness around the vehicle 1. Since the second emission units 204 of the auxiliary illumination unit 200 come close to the face of the driver as compared with the first emission units 104 of the image pickup unit 100, the emission intensity of the second emission units 204 is set to be lower as compared with the emission intensity of the first emission units 104.

Subsequently, the emission timing of the near infrared light of the first emission units 104 and the second emission units 204 is set (S106). In this process, timing at which the first emission units 104 and the second emission units 204 emit the near infrared light is set to match exposure timing of a solid-state imaging element not shown incorporated into the image pickup unit 102.

Figure 8:
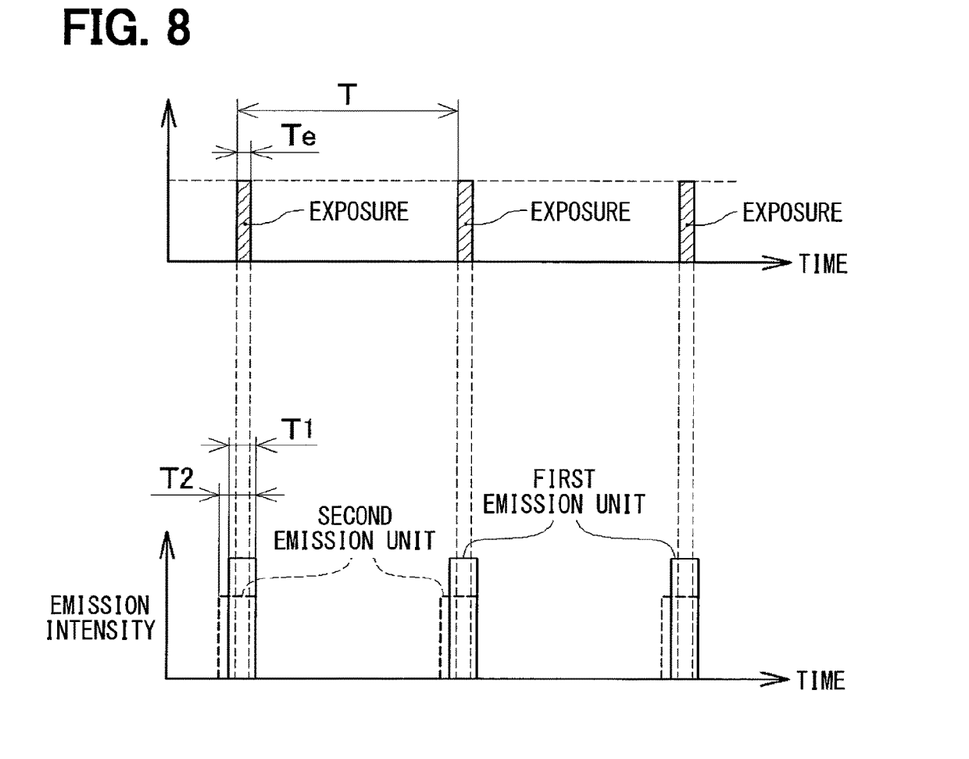
FIG. 8 is a diagram illustrating a state of setting an emission timing of a near infrared light in synchronism with exposure timing of the image pickup unit.

FIGS. 8A and 8B illustrate a state of setting the emission timing of the first emission units 104 and the second emission units 204 to match the exposure timing of the image pickup unit 102. As illustrated in FIG. 8A, the image pickup unit 102 opens a shutter only during a time Te at an interval of a predetermined period T (about 30 msec), and exposes the incorporated solid-state imaging element. In other words, since the light does not reach the solid-state imaging element during a period when the shutter is closed, there is no need to emit the near infrared light from the first emission units 104 of the image pickup unit 100 or the second emission units 204 of the auxiliary illumination unit 200. Under the circumstances, as illustrated in FIG. 8B, the first emission units 104 and the second emission units 204 according to the present embodiment emit pulsed near infrared light at the exposure timing of the image pickup unit 102. With the above configuration, since a time during which the near infrared light is actually emitted can be shortened, a power consumption in the first emission units 104 and the second emission units 204 can be suppressed. Further, the deterioration of the first emission units 104 and the second emission units 204 due to use can be suppressed.

In the present embodiment, the first emission units 104 and the second emission units 204 are set to start the emission of the near infrared light at timing slightly earlier than that when the image pickup unit 102 starts exposure. This is because a margin is provided for a case in which the timing at which the image pickup unit 102 starts the exposure is deviated for some reason, and because a possibility that the amount of near infrared light is not stable from the viewpoint of the characteristic of the circuit immediately after energization to the LEDs starts is considered. Also, the timing of the emission start in the second emission units 204 is set to be slightly earlier than that in the first emission units 104. This is because wiring to the second emission units 204 from the image pickup control unit 150 is longer than wiring to the first emission units 104 therefrom, and therefore a transmission delay of the signal due to that influence, and an influence of a detection delay of the signal by distortion of the signal waveform are considered. As described above, the timing of the first emission units 104 and the second emission units 204 are determined taking mounting positions and circuit configurations thereof into consideration. Further, in the present embodiment, the first emission units 104 and the second emission units 204 continue the emission of the near infrared light only during a slight period even after the image pickup unit 102 has terminated the exposure. This is because a margin is provided for a case in which the timing of an exposure termination in the image pickup unit 102 is deviated for some reason.

An exposure time Te in the image pickup unit 102 is determined by the image pickup control unit 150 according to an object of which an image to be captured or the surrounding brightness. Under the circumstances, as illustrated in FIG. 8B, emission timings T1 and T2 of the near infrared light in the respective first emission units 104 and second emission units 204 are set according to the exposure time Te (S106 in FIG. 7).

Subsequently, the image pickup control unit 150 detects the open/close state of the sunvisor 300 (S108). As described above with reference to FIG. 4, the open/close switch 310 is incorporated into the hinge 302 of the sunvisor 300, and it can be determined whether the sunvisor 300 is in the open state (state in which the sunvisor 300 is present at the light shielding position), or in the closed state (state at the storage position). If it is determined that the sunvisor 300 is in the open state (YESin S110), the emission intensity of the second emission units 204 which is set in S104 previously is suppressed (S112). Alternatively, the emission intensity may be suppressed without emission.

On the contrary, if it is determined that the sunvisor 300 is not in the open state (NO in S110), a process for suppressing the emission intensity of the second emission units 204 is not performed. When the sunvisor 300 is in the open state, a reason for suppressing the intensity of emitting the near infrared light by the second emission units 204 will be described later. When the sunvisor 300 is in the open state, the process for suppressing the intensity of emitting the near infrared light by the second emission units 204 is executed by the image pickup control unit 150. Therefore, in the present embodiment, the image pickup control unit 150 corresponds to an emission intensity suppression unit.

As described above, after the emission timing and the emission intensity of the near infrared light in the first emission units 104 and the second emission units 204 have been set (S104 to S112), the near infrared light is emitted from the first emission units 104 and the second emission units 204, and the shutter of the image pickup unit 102 is then opened to capture an image of the face of the driver (S114).

Then, the captured image of the face is transmitted to the monitoring control unit 160, and the monitoring control unit 160 analyzes the image of the face to detect the arousal level of the driver (S116). That is, face components such as eyes, a nose, and a mouth are detected from the image of the face to determine three dimensional positions of the face and an orientation of the face. Further, an image of the eyes is analyzed to detect a state of eyelids, thereby detecting the open/close state of the eyes. Then, a frequency at which the driver opens and closes the eyelids, and a time during which the driver closes the eyelids are detected according to the analysis result of the images captured in a past predetermined period (for example, 30 minutes), to thereby detect the arousal level of the driver. Thereafter, the monitoring control unit 160 determines whether the arousal level of the driver decreases, or not (S118). Then, if the arousal level decreases (YES in S118), the driver is warned about the decrease in the arousal level through a method for, for example, outputting an alarm sound from a speaker not shown which is mounted on the vehicle 1 (S120). Thereafter, the process returns to S100 to continue the monitoring of the driver. On the contrary, if the arousal level does not decrease (NO in S118), the process returns to S100 as it is without warning about the decrease in the arousal level, and continues the monitoring of the driver.

In order to monitor the arousal level of the driver with high precision in the driver state monitoring process, it is important that the image of the face of the driver can be captured under the stable condition regardless of a difference in the weather or the time zone. In the image pickup device 10 according to the present embodiment, the image of the face of the driver can be captured under the stable condition, despite the simple structure. This configuration will be described below.

Figure 9:
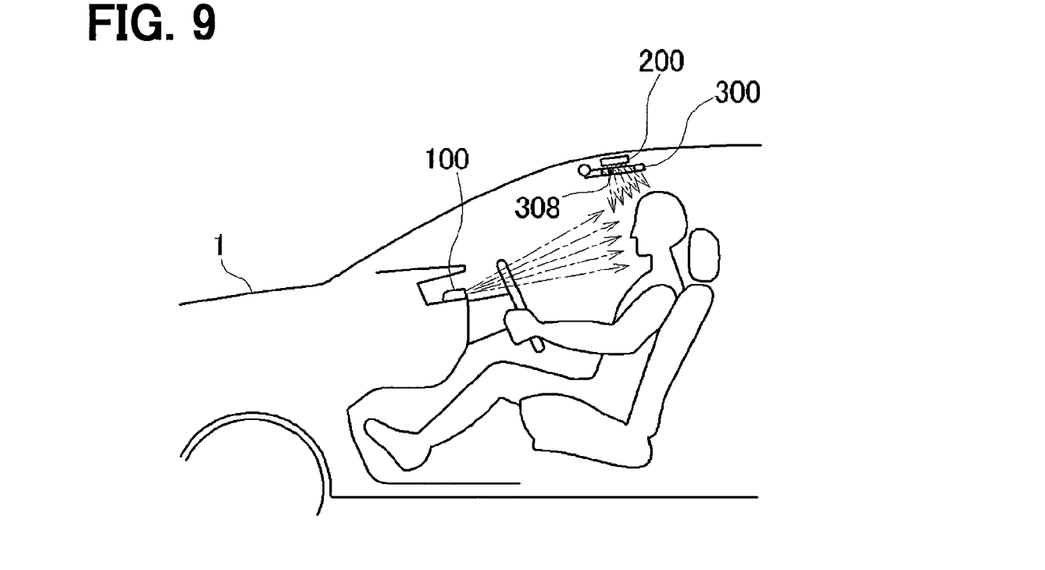
FIG. 9 is a diagram illustrating a state of emitting the near infrared light from the auxiliary illumination unit over the sunvisor in a state where the sunvisor is present at a storage position.

FIG. 9 illustrates a state in which the near infrared light is emitted toward the face of the driver when the sunvisor 300 is in the closed state (state at the storage position). As described above, the first emission units 104 (see FIG. 2) is incorporated into the image pickup unit 100, and the near infrared light is emitted from the first emission units 104 diagonally upward toward the face of the driver. The second emission units 204 (see FIG. 3) is incorporated into the auxiliary illumination unit 200 disposed above the driver, and the near infrared light emitted from the second emission units 204 transmits the transmission windows 308 (see FIG. 4) disposed in the sunvisor 300, and is emitted toward the face of the driver from the upper side.

Arrows indicated by thin one-dot chain lines in FIG. 9 represent a state in which the near infrared light is emitted toward the face of the driver from the first emission units 104 in the image pickup unit 100 and the second emission units 204 in the auxiliary illumination unit 200. As shown in the figure, since the near infrared light can be emitted from the respective diagonally lower and upper sides of the face of the driver, the overall face can be always illuminated under the stable condition. As a result, the image of the face of the driver can be captured under the stable condition without being affected by the weather or the time zone.

As illustrated in FIG. 3, the auxiliary illumination unit 200 is equipped with not only the second emission units 204 that emit the near infrared light, but also the illumination unit 202 that emits the visible light. The illumination unit 202 is mainly used for the driver to confirm maps or documents, or for a woman driver to fix makeup with the small mirror 306 attached to the sunvisor 300. The illumination unit 202 is mounted on most of the vehicles 1. The lighting control of the auxiliary illumination unit 200 is always performed by the switching operation of the driver. This is because the discrimination of whether the dazzled driver opens the sunvisor 300, or the driver wishes to see his face reflected on the small mirror 306 is difficult.

Then, the second emission units 204 according to the present embodiment are mounted on the auxiliary illumination unit 200 together with the illumination unit 202. Therefore, the second emission units 204 can be assembled by the workload for assembling the illumination unit 202 into the vehicle 1. If a harness for supplying a power to the illumination unit 202 is integrated with a harness for supplying a power to the second emission units 204, the number of harnesses assembled into the vehicle 1 does not increase. Thus, although the auxiliary illumination unit 200 having the illumination unit 202 becomes slightly larger, and the harness to the illumination unit 202 becomes slightly thicker, the structure of the vehicle 1 is not complicated, and the workload for assembling the auxiliary illumination unit 200 into the vehicle 1 does not increase.

Further, in the sunvisor 300, since the plate-like near infrared light transmission filter is merely fitted into the sunvisor 300 to provide the transmission windows 308, the structure of the sunvisor 300 can be held to be simple.

For the above-mentioned reasons, in the image pickup device 10 according to the present embodiment, the near infrared light can be emitted to the overall face of the driver under the stable condition without being affected by a difference in the weather or the time zone. In addition, the structure is simple, and the workload for assembling into the vehicle 1 does not increase.

Also, in the image pickup device 10 according to the present embodiment, the transmission windows 308 that do not transmit the visible light, but transmit the partial wavelength of the near infrared light are disposed in the sunvisor 300. Therefore, when the sunvisor 300 is in the open state (light shielding position), the emission intensity of the near infrared light from the second emission units 204 is suppressed to enable a reduction in the power consumption. This is due to the following reasons.

The reason that the driver puts the sunvisor 300 into the open state to shield the visible light from the sunlight is because the sunlight has intensity as much as the driver feeds dazzled, and illuminates the upper side of the face of the driver directly. The sunvisor 300 according to the present embodiment is provided with the transmission windows 308 that transmit the partial wavelength of the near infrared light. Therefore, even if the driver puts the sunvisor 300 into the open state to shield the visible light from the sunlight, the partial wavelength of the near infrared light contained in the sunlight is transmitted through the transmission windows 308, and is emitted to the upper side of the face of the driver.

Figure 10:
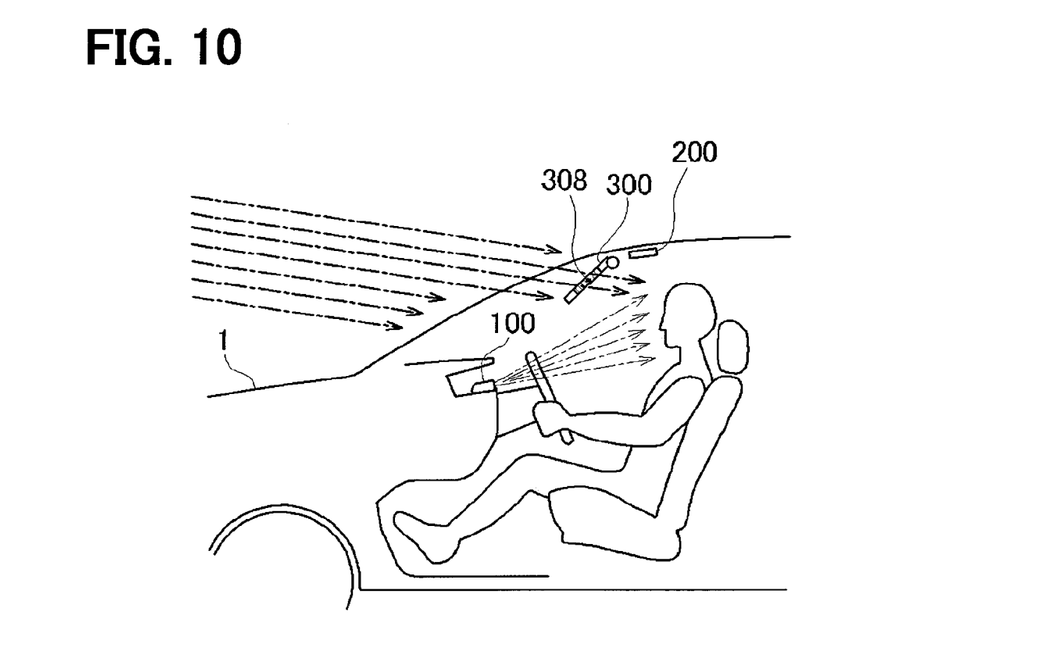
FIG. 10 is a diagram illustrating why an emission intensity of the near infrared light from the auxiliary illumination unit can be suppressed in a state where the sunlight is shielded with the sunvisor.

Arrows of thick one-dot chain lines illustrated in FIG. 10 represent a state in which the light of the partial wavelength of the near infrared light contained in the sunlight is transmitted through the transmission windows 308 of the sunvisor 300 to illuminate the upper side of the face of the driver. In addition, since the sunlight is strong enough to make the sunvisor 300 in the open state, the near infrared light that is transmitted through the transmission windows 308 also has a sufficient amount of light. Thus, even if the emission intensity of the near infrared light from the second emission units 204 of the auxiliary illumination unit 200 is suppressed (or emission ceases), the overall face of the driver can be illuminated with the near infrared light. As a result, the power consumption can be reduced as much as the emission of the near infrared light from the second emission units 204 is suppressed (or ceases). The near infrared light is transmitted through the transmission windows 308 of the sunvisor 300, and is emitted to the upper side of the face of the driver. However, since most of the visible light is not transmitted through the transmission windows 308, the driver does not feel dazzled.

There are plural modifications of the image pickup device 10 according to the present embodiment described above. Hereinafter, differences of the present embodiment from those modifications will be mainly described. The same parts as those in the present embodiment described above are denoted by identical reference numerals, and the detailed description will be omitted.

First Modification

In the above-mentioned embodiment, if the sunvisor 300 is in the open state (state at the light shielding position), it is determined that the driver shields the visible light from the sunlight, and the emission intensity of the near infrared light from the second emission units 204 of the auxiliary illumination unit 200 is suppressed. However, the driver puts the sunvisor 300 into the open state not only in a case to shield the visible light from the sunlight, and it is conceivable that the driver puts the sunvisor 300 into the open state when the driver sees the small mirror 306 disposed in the sunvisor 300, or when the driver holds a card or a receipt in the sunvisor 300. Under the circumstances, in this case, the following process may be conducted so as not to suppress the emission intensity from the second emission units 204.

Figure 11:
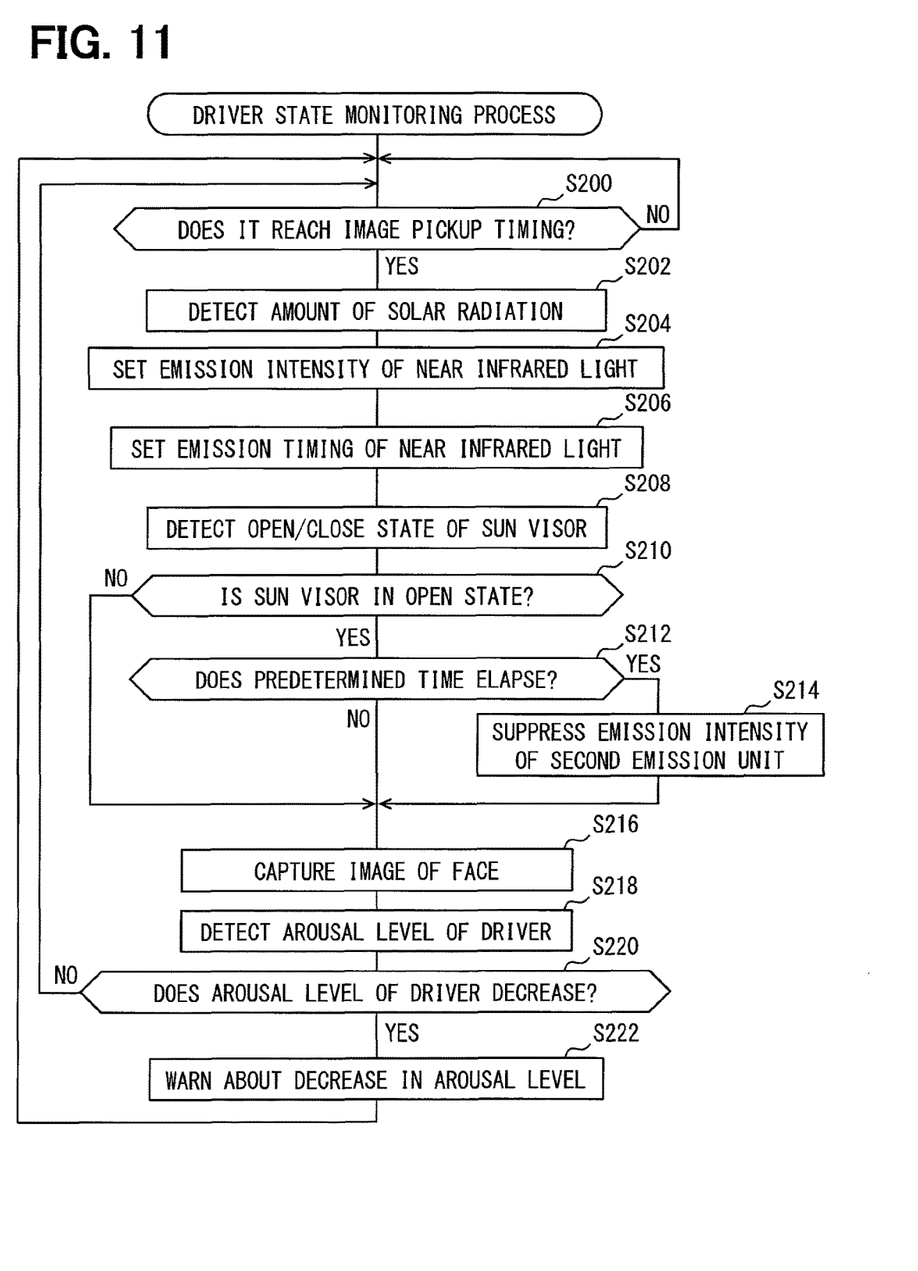
FIG. 11 is a flowchart illustrating a driver state monitoring process according to a first modification.

FIG. 11 illustrates a flowchart of a driver state monitoring process according to a first modification. This process is largely different from the driver state monitoring process described above with reference to FIG. 7 in that not only whether the sunvisor 300 is in the open state, or not, but also an elapsed time after the sunvisor 300 becomes in the open state is also considered. Hereinafter, the process will be described in brief. First of all, it is determined whether it is image pickup timing of the driver, or not (S200), and if it is the image pickup timing (YES in S200), the amount of solar radiation is detected (S202). Then, the emission intensity and the emission timing of the near infrared light in the first emission units 104 and the second emission units 204 are set on the basis of the amount of solar radiation (S204, S206).

Subsequently, the open/close state of the sunvisor 300 is detected (S208), and it is determined whether the sunvisor 300 is in the open state, or not (S210). As a result, if the sunvisor 300 is not in the open state (no in S210), the near infrared light is emitted with the emission intensity set in S204 from the first emission units 104 and the second emission units 204 to capture the image of the face of the driver (S216).

On the contrary, if the sunvisor 300 is in the open state (YES in S210), it is determined whether a predetermined time elapses after the sunvisor 300 has become in the open state, or not, in the first modification (S212). The predetermined time is set to a time (typically about 5 to 10 seconds) to the extent required for the driver to take look into the small mirror 306 of the sunvisor 300, or to hold a card or a receipt in the sunvisor 300.

If the open state is still continued even when the predetermined time elapses after the sunvisor 300 has become in the open state (that is, YES in S212), it is conceivable that the driver does not temporarily put the sunvisor 300 into the open state for some reason, but puts the sunvisor 300 into the open state for the purpose of shielding the visible light from the sunlight. Therefore, the emission intensity of the near infrared light from the second emission units 204 is suppressed (S214). Alternatively, the emission intensity may be suppressed by ceasing the emission of the near infrared light. On the other hand, if the predetermined time does not elapse after the sunvisor 300 has become in the open state (no in S212), since there is the possibility that the driver temporarily puts the sunvisor 300 into the open state for some reason. Therefore, the emission intensity of the second emission units 204 remains set in S204.

The subsequent processes are identical with the driver state monitoring process described above. That is, the near infrared light is emitted with the set emission intensity from the first emission units 104 and the second emission units 204, and the shutter of the image pickup unit 102 is opened to capture the image of the face of the driver (S216). Then, the captured image of the face is analyzed to detect the arousal level of the driver (S218), and if the arousal level of the driver decreases (YES in S220), the driver is warned about the decrease in the arousal level (S222). On the contrary, if the arousal level does not decrease (NO in S220), the process returns to S200 as it is without warning about the decrease in the arousal level, and continues the monitoring of the driver.

In the driver state monitoring process according to the first modification described above, even if the driver puts the sunvisor 300 into the open state only for a short time for the purpose other than the shielding of the sunlight, the emission intensity of the near infrared light from the second emission units 204 is not suppressed. Thus, since the emission intensity of the near infrared light to the upper side of the face of the driver is not short, an excellent image of the face can be captured to detect the arousal level of the driver. It is needless to say that even if the driver puts the sunvisor 300 into the open state for the purpose of shielding the sunlight, the emission intensity of the second emission units 204 is maintained during a period when the predetermined time elapses. However, even in this case, there is no change in that the sufficient near infrared light is emitted to the upper portion of the face of the driver. Thus, the arousal level of the driver can be detected by analyzing the obtained image of the face.

Second Modification

In the embodiment and the modification described above, the plate-like near infrared light transmission filter is fitted into the main body part 304 of the sunvisor 300 to form the transmission windows 308. Alternatively, the main body part of the sunvisor may be formed of the near infrared light transmission filter.

Figure 12:
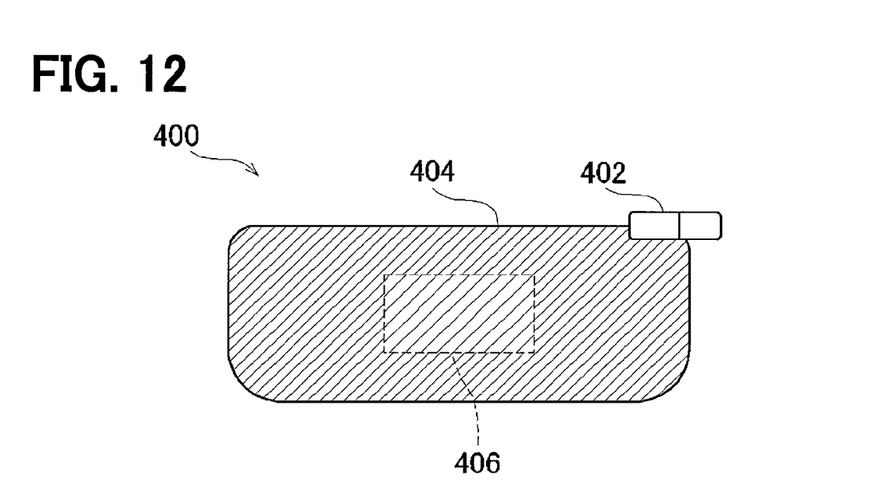
FIG. 12 is a diagram illustrating a sunvisor according to a second modification.

FIG. 12 exemplifies a sunvisor 400 in the second modification. In the example shown, a main body part 404 of the sunvisor 400 is formed of a near infrared light transmission filter made of, for example, methacrylic resin. The sunvisor 400 can rotate around a portion of a hinge 402, and a small mirror 406 using a cold mirror is formed in the center of a surface facing the driver when the sunvisor 400 rotates and puts into an open state. In the present specification, "cold mirror" is an optical thin film formed by depositing a dielectric multilayer film, and has the characteristics of transmitting the infrared light, but reflecting the visible light.

In the sunvisor 400 according to the second modification described above, when the sunvisor 400 is put into the open state for the purpose of shielding the sunlight, since a partial wavelength of the near infrared light is transmitted from an extensive range of the sunvisor 400, the upper portion of the face of the driver can be emitted with a sufficient amount of near infrared light. As a result, the excellent image of the face can be captured by emitting the near infrared light to the overall face together with the near infrared light from the first emission units 104 of the image pickup unit 100. Also, when, for example, a woman driver confirms makeup, since the small mirror 406 using the cold mirror is formed, the confirmation of makeup or the correction of makeup can be performed.

Third Modification

In the embodiments and the modifications described above, both of the sunvisors 300 and 400 are switched between the open state (light shielding position) and the closed state (storage position) by rotating the main body parts 304 and 404. Alternatively, a sunvisor of the type in which the main body parts 304 and 404 are not rotated but slid to switch between the open state (light shielding position) and the closed state (storage position) can be provided.

Figure 13A:
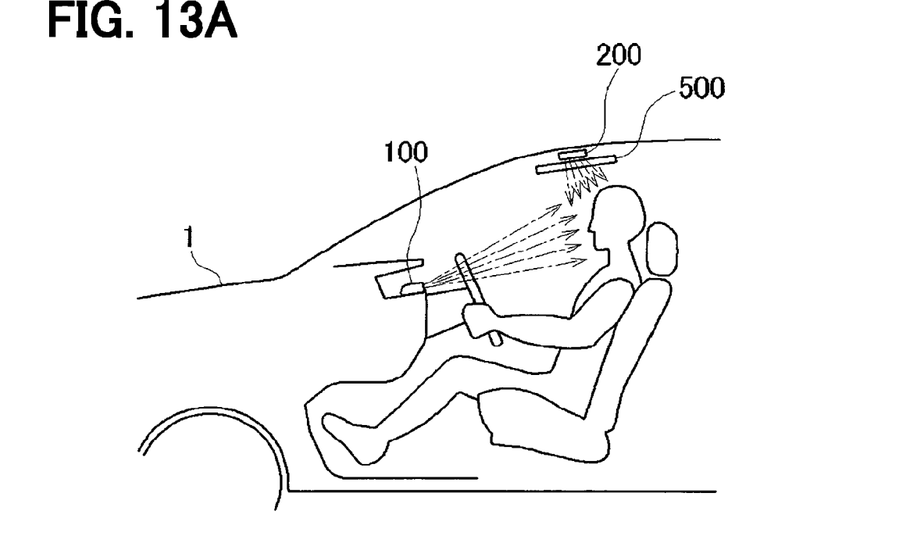
FIG. 13A is a diagram illustrating a state in which a slide sunvisor according to the third modification is present at a storage position.
Figure 13B:
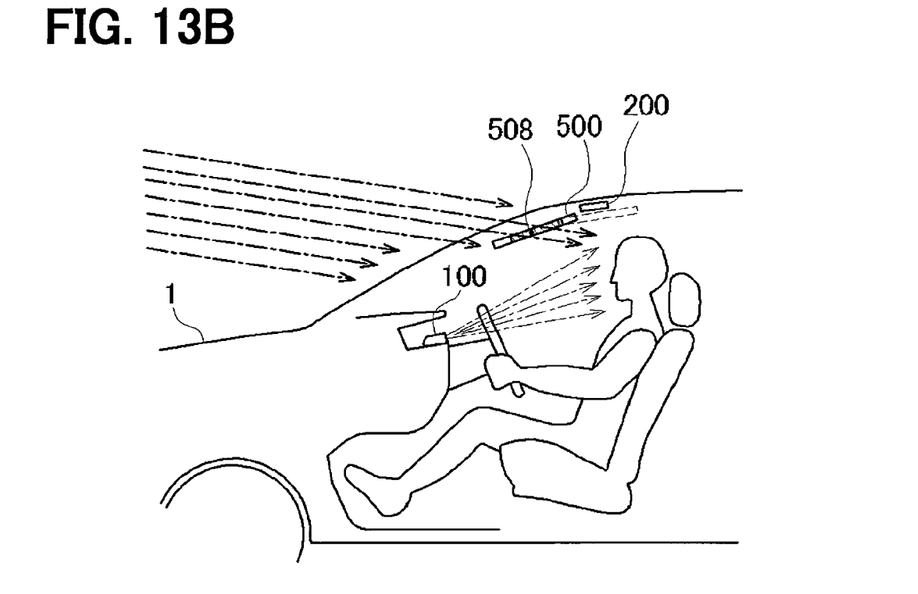
FIG. 13B is a diagram illustrating a state in which the slide sunvisor according to the third modification is present at a light shielding position.

FIGS. 13A and 13B exemplify a third modification using a sunvisor 500 of the slide type. For example, in a state where the sunvisor 500 of the slide type is at a storage position, a transmission window 508 using a near infrared light transmission filter is disposed in a portion facing the second emission units 204 (see FIG. 3) of the auxiliary illumination unit 200. With the above configuration, as illustrated in FIG. 13A, when the sunvisor 500 is at the storage position, the upper portion of the face of the driver can be emitted with the near infrared light from the second emission units 204 (see FIG. 3) of the auxiliary illumination unit 200. As a result, the overall face of the driver can be illuminated with the near infrared light together with the near infrared light from the first emission units 104 (see FIG. 2) of the image pickup unit 100, and the excellent image of the face can be captured.

Also, as illustrated in FIG. 13B, when the driver sets the sunvisor 500 at the light shielding position for the purpose of shielding the sunlight, since the light of a partial wavelength of the near infrared light contained in the sunlight is transmitted through the transmission window 508, the upper portion of the face of the driver is illuminated with the transmitted near infrared light. Arrows of thick one-dot chain lines illustrated in the figure represent a state in which the light of the partial wavelength of the near infrared light contained in the sunlight illuminates the upper side of the face of the driver. Thus, the overall face of the driver can be illuminated with the near infrared light together with the near infrared light from the first emission units 104 (see FIG. 2) of the image pickup unit 100, and the excellent image of the face can be captured.

The present embodiment and the modifications have been described above, but the present invention is not limited to the above embodiment and modifications, and can be variously implemented without departing from the spirit of the invention.

The invention claimed is:

1. An image pickup device that is mounted on a vehicle and captures an image of a driver of the vehicle, comprising:
a face image pickup unit arranged in front of a driver seat of the vehicle, and capturing an image of a face of the driver from a front side of the driver;
a first light transmitting source arranged in front of the driver seat of the vehicle, and emitting a near infrared light toward the face from a front lower side of the driver;
a sunvisor fitted to an upper side of the driver seat in a vehicle interior, and being movable between a light shielding position at which sunlight to the face is shielded and a storage position at which the sunlight to the face is not shielded; and
a second light transmitting source located at a position to be covered with the sunvisor when the sunvisor is present at the storage position and not to be covered with the sunvisor when the sunvisor is present at the light shielding position, and emitting the near infrared light toward the face of the driver, wherein
the sunvisor includes a near infrared light transmitting portion covering the second light transmitting source when the sunvisor is located at the storage position which is made of a material that shields a visible light contained in the sunlight and transmits the near infrared light;
a sunvisor position switch configured as open when the sunvisor is present at the light shielding position and as closed when the sunvisor is present in the storage position; and
an image pickup control processor containing a microprocessor configured
to suppress an intensity of the near infrared light emitted by the second light transmitting source when the sunvisor position switch is open and the sunvisor is at the light shielding position which enables the near infrared light to pass through the near infrared light transmitting portion of the sunvisor,
to not suppress an intensity of the near infrared light by the second light transmitting source when the sunvisor position switch is closed and the sunvisor is present at the storage position,
to determine a duration time that elapses after the sunvisor is present at the light shielding position,
to determine that the sunvisor is present at the light shielding position for shielding the visible light contained in the sunlight and suppress an intensity of the near infrared light emitted by the second light transmitting source when the duration time is equal to or longer than a predetermined period of time, and
to determine that the sunvisor is present at the light shielding position not for shielding the visible light contained in the sunlight and not suppress an intensity of the near infrared light emitted by the second light transmitting source when the duration time is shorter than the predetermined period of time.

2. The image pickup device according to claim 1, wherein
the face image pickup unit captures the image of the face with a predetermined period, and
at least one of the first light transmitting source and the second light transmitting source emits the near infrared light in synchronism with the period when the face image pickup unit captures the face.

3. A near infrared light emission device that is mounted on a vehicle and emits a near infrared light toward a face of a driver of the vehicle, comprising:
a first light transmitting source arranged in front of the driver seat of the vehicle and emitting the near infrared light toward the face from a front lower side of the driver;
a sunvisor fitted to an upper side of the driver seat in a vehicle interior, and being movable between a light shielding position at which sunlight to the face is shielded and a storage position at which the sunlight to the face is not shielded; and a second light transmitting source located at a position to be covered with the sunvisor when the sunvisor is present at the storage position, and not to be covered with the sunvisor when the sunvisor is present at the light shielding position, and emitting the near infrared light toward the face of the driver, wherein the sunvisor includes a near infrared light transmitting portion covering the second light transmitting source when the sunvisor is located at the storage position which is made of a material that shields a visible light contained in the sunlight and transmits the near infrared light;

a sunvisor position switch configured as open when the sunvisor is present at the light shielding position and as closed when the sunvisor is present in the storage position; and an image pickup control processor configured to suppress an intensity of the near infrared light emitted by the second light transmitting source when the sunvisor position switch is open and the sunvisor is at the light shielding position which enables the near infrared light to pass through the near infrared light transmitting portion of the sunvisor, to not suppress an intensity of the near infrared light by the second light transmitting source when the sunvisor position switch is closed and the sunvisor is present at the storage position, to determine a duration time that elapses after the sunvisor is present at the light shielding position, to determine that the sunvisor is present at the light shielding position not for shielding the visible light contained in the sunlight and suppress an intensity of the near infrared light emitted by the second light transmitting source when the duration time is equal to or longer than a predetermined period of time, and to determine that the sunvisor is present at the light shielding position not for shielding the visible light contained in the sunlight and not suppress an intensity of the near infrared light emitted by the second light transmitting source when the duration time is shorter than the predetermined period of time.

4. The image pickup device according to claim 1, wherein the near infrared light from the sunlight passes through the near infrared light transmitting portion of the sunvisor when the sunvisor position switch is open and the sunvisor is at the light shielding position.

5. The near infrared light emission device according to claim 3, wherein the near infrared light from the sunlight passes through the near infrared light transmitting portion of the sunvisor when the sunvisor position switch is open and the sunvisor is at the light shielding position.

6. A sunvisor that is to be fitted to a vehicle interior of a vehicle comprising:

a main body part that is made of a material shielding a visible light and transmitting a near infrared light; and an attaching part that is to attach the main body part to the vehicle interior in a state to be movable between a light shielding position and a storage position, the light shielding position being a position at which the main body part shields a visible light contained in the sunlight and transmits a near infrared light contained in the sunlight, the storage position being a position at which the main body part does not shield the visible light contained in the sunlight, wherein the main body part has a cold mirror that is made of a dielectric multilayer film transmitting a near infrared light and reflecting a visible light, the cold mirror is provided on a surface of the main body part facing a driver seat of the vehicle when the main body part is in the light shielding position, and when the main body part is in the light shielding position, the cold mirror reflects a visible light from the vehicle interior toward the driver seat of the vehicle.

7. The sunvisor according to claim 6, wherein when the main body part is in the light shielding position, the main body part and the cold mirror transmit the near infrared light contained in the sunlight toward the driver seat of the vehicle.

* * * * *